United States Patent [19]
Pelletier et al.

[11] Patent Number: 5,779,942
[45] Date of Patent: Jul. 14, 1998

[54] LONG-CHAIN DIALKYLMAGNESIUM, ITS PREPARATION PROCESS AND APPLICATIONS

[75] Inventors: Jean-François Pelletier, La Garde; Karel Bujadoux, Dunkerque; Xavier Olonde, Neuville en Ferrain; Emmanuel Adisson, Arques; André Mortreux, Hem; Thomas Chenal, Villeneuve d'Ascq, all of France

[73] Assignees: Enichem S.p.A., Milan, Italy; Universite des Sciences et Technologies de Lille, Villeneuve d'Ascq, France

[21] Appl. No.: 628,373

[22] Filed: Apr. 5, 1996

[30] Foreign Application Priority Data

Apr. 7, 1995 [FR] France ................... 95 04203

[51] Int. Cl.$^6$ ........................................ C07F 3/02
[52] U.S. Cl. ................... 260/665 R; 260/665 G; 568/671; 568/672
[58] Field of Search .............. 260/665 G, 665 R; 568/671, 672

[56] References Cited

U.S. PATENT DOCUMENTS

| | | |
|---|---|---|
| 3,450,735 | 6/1969 | Lundeen et al. |
| 3,670,038 | 6/1972 | Shepherd, Jr. |
| 3,737,393 | 6/1973 | de Vries ................ 260/665 G |
| 3,766,280 | 10/1973 | Kamienski et al. ....... 260/665 G |
| 4,127,507 | 11/1978 | Fannin et al. ........... 260/665 G X |

OTHER PUBLICATIONS

Bogdanovic et al., "Diorganomagnesium Compounds from Magnesium, Hydrogen, and 1-Alkenes and Their Application in Synthesis", Chem. Ber., 126:1371–1383 (1993).

*Primary Examiner*—Paul F. Shaver
*Attorney, Agent, or Firm*—Finnegan, Henderson, Farabow, Garrett & Dunner L.L.P.

[57] ABSTRACT

This dialkylmagnesium is represented by the formula R—($CH_2$—$CH_2$)$_n$—Mg—($CH_2$—$CH_2$)$_{n'}$—R', (E—O—E')$_x$ where R and R' each independently represent a $C_1$-$C_{20}$ hydrocarbon residue, branched or not, substituted or not, of the alkyl, cycloalkyl or aralkyl type; n and n', identical or substantially identical, represent an average number of —$CH_2$—$CH_2$— linkages such that the average number of carbon atoms in each of the two chains borne by Mg is greater than 20; E and E', identical or different, each represent an alkyl radical, linear or cyclical, branched or not; and $0 \leq x \leq 2$, x being the average value of the number of moles of E—O—E' ether complexed to the dialkylmagnesium. In order to prepare a dialkylmagnesium of this type, ethylene is polymerized in an anhydrous, de-oxygenated hydrocarbonaceous solution by means of a catalyst Cp*$_2$MCl$_2$Li(OEt$_2$)$_2$ (Cp*=a pentamethylcyclopentadienyl ligand; M=scandium, yttrium or a metal of the lanthanide series; Et=ethyl), in the presence of a dialkylmagnesium, soluble in the solvent, of the formula R—Mg—R', (E—O—E')$_x$ where R, R', E, E' and x are as defined above, as a chain-transfer agent, and the reaction is stopped before the polydispersity of the polymer product obtained exceeds 2, and preferably before it exceeds 1.5.

19 Claims, No Drawings

LONG-CHAIN DIALKYLMAGNESIUM, ITS PREPARATION PROCESS AND APPLICATIONS

The present invention relates to a long-chain dialkylmagnesium, to a process for its preparation and to its applications.

It is well known that the reaction of making multiple ethylene or α-olefin insertions in a metal-carbon bond can be carried out quickly and easily with transition metals of groups III to VIII of the periodic table. The resulting applications, such as polymerization and oligomerization, are currently widely used in the industrial context. The products thus manufactured are the higher α-olefins and either linear or branched hydrocarbon chains of extremely high molecular mass. However, the chemical reactivity of these products is heavily reduced because the extremities of these hydrocarbon chains are no longer bound to the metal on which they grew.

Among other metals the case of aluminum is of interest. The reaction of the trialkylaluminum (AlEt$_3$, for example) with ethylene, discovered by K. Ziegler, is better known by the term "Aufbau" reaction. This reaction is generally carried out at moderate ethylene pressures and at temperatures above 115° C. The reaction conditions determine the nature of the products:

- terminal olefins are synthesized at temperatures at which a reaction of β hydrogen elimination is frequent. The growth and termination of chains take place at comparable rates. Typically the reaction takes place at 200°–250° C. and at ethylene pressures of 130–150 bar. Most of the products are linear α-olefins containing 4 to 8 carbon atoms;
- heavy trialkylaluminums are formed at 115°–130° C. and at 135 bar (American patent U.S. Pat. No. 3,450,735). The reaction products of the AlRR'R" type have chain lengths with a statistical distribution ranging from 6 to 14 carbon atoms. Their main application is the oxidation of these heavy trialkylaluminiums to produce fatty alcohols used in the detergent industry.

Another process for the synthesis of heavy trialkylaluminums, recently perfected, is described in European patent application EP-A-0 574 854. The ethylene oligomerization reaction is carried out by a catalytic method by metallocenic compounds based on metals of the actinide group (Cp*$_2$UCl$_2$; Cp*=pentamethylcyclopentadienyl), activated by an aluminoxane or a non-co-ordinating agent of the class of perfluoroborates. As the chains grow they are transferred to the aluminum which is present in the form of AlR$_3$. The distribution of the heavy alkyaluminums thus produced generally follows a Poisson distribution. Their chain lengths range from 4 to 22 carbon atoms.

The reaction is carried out at temperatures between 0° and 100° C. and pressures between 0 and 70 bar for a period of between 10 and 40 minutes. The advantages cited for this operating method are the use of less extreme conditions and the higher purity of the products, since it substantially reduces the formation of polyethylene as a by-product formed by the reaction of β hydrogen elimination.

As for magnesium, the dialkylmagnesiums are generally prepared by dismutation or by the alkylation of Grignard compounds.

The reaction of oligomerizing ethylene with dialkylmagnesiums (the analogue of the Aufbau reaction described above) is described by D. B. Malpass in J. Organomet. Chem., Library (1980), 9, 1 and by H. G. Richey in Inorganic Reactions and Methods (Ed.: A. P. Hogen), VCH, New York, (1989), vol. 10, section 5.4.2.5.1. It permits the production of a statistical mixture of dialkylmagnesiums with chain lengths between 4 and 20 carbon atoms. Reaction conditions are 120° C., 150 bar of ethylene for 12 hours. Moreover the presence of a strong base such as quinuclidine in a stoichiometric quantity is necessary. By-products (α-olefins) are generated simultaneously, representing about 15% of the compounds. Moreover the strong base is subsequently found to be mixed (or complexed) with the reaction products, necessitating costly purification processes. Moreover the alkyl chain length is limited by the termination reactions (β hydrogen elimination); the formation of heavy dialkylmagnesiums would require the use of higher pressures.

B. Bogdanovic et al. (Chem. Ber., (1993), 126, 1371–1383) have recently optimized "hydromagnezation", which consists in synthesizing the dialkylmagnesiums from MgH$_2$ and an α-olefin in the presence of a catalyst (MtCl$_4$, Mt representing a metal of group IVb of the periodic table). The reaction takes place in two stages:

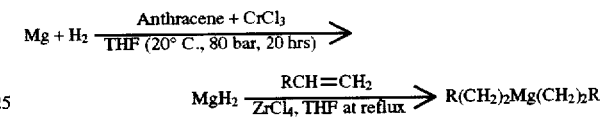

Despite a complex stage for the synthesis of the intermediate MgH$_2$, the advantages cited by B. Bogdanovic et al. are defined in terms of better yields and a more economical process. However, the lengths of the alkyl chains bound to the magnesium are determined by the size of α-olefins used for synthesis. These lengths do not exceed 20 carbon atoms.

The present inventors concentrated on dialkylmagnesiums, which are more suitable than the equivalent alkylaluminums for carrying out valorization reactions. They discovered that the ethylene can be polymerized by means of a particular lanthanide-based compound as the catalyst, subsequently transferring the growing chains to the magnesium of a dialkylmagnesium intervening as a highly efficient transfer agent. Moreover they discovered that the temperature and pressure conditions of this reaction are more favourable than those advocated by D. B. Malpass and H. G. Richey, and by B. Bogdanovic et al. (see above), with substantially reduced reaction times. Moreover the characteristics of the chains bound to the magnesium (molecular mass and polydispersity) are easily monitored by the synthesis conditions. The mixture of reaction products obtained is characterized by a very narrow statistical distribution which is favorable to the various proposed applications.

The first subject of the present invention is thus a long-chain dialkylmagnesium represented by the following formula (I):

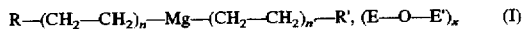

wherein:

R and R' each independently represent a C$_1$–C$_{20}$ hydrocarbon residue, branched or not, substituted or not, of the alkyl, cycloalkyl or aralkyl type;

n and n', identical or substantially identical, represent an average number of —CH$_2$—CH$_2$— linkages such that the average number of carbon atoms in each of the two chains borne by Mg is greater than 20, and in particular is greater than 40;

E and E', identical or different, each represent an alkyl radical, linear or cyclical, branched or not; and $0 \leq x \leq 2$, x being the average value of the number of moles of E—O—E' ether complexed to the dialkylmagnesium.

As examples of alkyl residues entering into the definition of R and R', one may cite methyl, ethyl, n-propyl, n-butyl, s-butyl, t-butyl and n-hexyl residues.

The average number of carbon atoms in each of the two chains borne by Mg is, as indicated, generally greater than 20. In fact this number can reach 300 or even 500.

E—O—E' represents an ether complexed to the actual dialkylmagnesium.

As examples of such ethers, one may cite diethyl ether, methyl isobutyl ether, di-n-butyl ether and di-isoamyl ether.

In general one may cite alkyl radicals $C_2$-$C_5$ as examples illustrating E and E'.

These dialkylmagnesiums of formula (I) should preferably have a polydispersity index $\overline{Mw}/\overline{Mn}$ between 1.1 and 2 or, even better, between 1.1 and 1.5.

A further subject of the present invention is a process for preparing a dialkylmagnesium represented by the following formula (I):

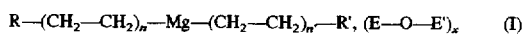

where:
- R and R' each independently represent a $C_1$-$C_{20}$ hydrocarbon residue, branched or not, substituted or not, of the alkyl, cycloalkyl or aralkyl type;
- n and n', identical or substantially identical, represent an average number of —$CH_2$—$CH_2$— linkages such that the average number of carbon atoms in each of the two chains borne by Mg is greater than 2;
- E and E', identical or different, each represent an alkyl radical, linear or cyclical, branched or not; and
- $0 \leq x \leq 2$, x being the average value of the number of moles of E—O—E' ether complexed to the dialkylmagnesium, characterized by the fact that ethylene is polymerized in an anhydrous, de-oxygenated hydrocarbonaceous solvent by means of a catalyst represented by formula (II):

$$Cp*_2MCl_2Li(OEt_2)_2 \qquad (II)$$

in which:
- Cp* represents a pentamethylcyclopentadienyl ligand;
- M is scandium, yttrium or a metal of the lanthanide series; and
- Et represents ethyl, in the presence of a dialkylmagnesium, soluble in the solvent, represented by formula (III):

in which R, R', E, E' and x are as defined below as a chain-transfer agent;
and by the fact that the reaction is stopped before the polydispersity of the polymer product obtained exceeds 2, preferably 1.5.

N-butylethylmagnesium may be cited as one possible dialkylmagnesium of formula (III). Others which may be equally well cited are di-n-hexylmagnesium or a soluble dialkylmagnesium conforming to formula (I) (just defined) and prepared by the process just described, the R—($CH_2$—$CH_2$)$_n$— and R'—($CH_2$—$CH_2$)$_n$— branches of the dialkylmagnesium (I) being the R— and R'— branches of the dialkylmagnesium (III).

The term R—Mg—R', (E—O—E')$_x$ with x>0 means that an ether E—O—E' has been complexed to the actual dialkylmagnesium. If the dialkylmagnesium would be insoluble in the reaction medium, adding ether allows it to dissolve in the form of solvent (III) with x>0. In this case the ether remains complexed to the final product of formula (I) with x>0.

Samarium, neodymium and yttrium may be cited as the metal M of the catalyst (II).

The molar ratio Mg/M should be advantageously between 5 and 10,000, preferably between 30 and 1000.

The hydrocarbonaceous solvent used for the reaction may be an aliphatic hydrocarbon, linear or cyclical, saturated or unsaturated, such as heptane, cyclohexane, decaline or isodecane; or a mixture of heavy alkanes ($C_9$-$C_{12}$), such as ISOPAR L, or an aromatic hydrocarbon, substituted or not, such as toluene, xylene or mesitylene.

According to the invention the reaction is carried out in moderate pressure and temperature conditions, ranging respectively between 1 and 10 bar (particularly between 1 and 2 bar) and between 20° and 120° C. (particularly between 40° and 80° C.). The duration of the reaction depends on the ratio Mg/M; it is generally between 2 minutes and 100 hours, particularly between 1 and 3 hours.

Generally it is desirable to stop the reaction prior to or at the point when a precipitate corresponding to a clear increase in the ethylene consumption appears.

As will be shown later, the first stage of the reaction (prior to the appearance of a precipitate) corresponds to the reaction of formation of the dialkylmagnesiums of formula (I), while the second stage corresponds to the production of polyethylene. In order to produce dialkylmagnesiums free of polyethylene it is therefore necessary to stop the reaction before the appearance of the second stage.

The length of the —($CH_2$—$CH_2$)$_n$— or —($CH_2$—$CH_2$)$_{n'}$ chains is a function of the operating conditions, more particularly of the ratio Mg/M and the reaction time.

A further subject of the present invention is a process for the polymerization of at least one polar monomer on the dialkylmagnesium of formula (I) as defined above or prepared by the process defined above as macroinitiator.

Polar monomers are particularly selected from the (meth) acrylic monomers such as alkyl (methyl, ethyl, isopropyl, isobutyl etc) methacrylates; (meth)acrylonitrile; vinyl pyridines such as vinyl-4 pyridine; and the lactones such as ε-caprolactone.

Polymerization of polar monomer(s) is generally carried out in solution in a hydrocarbonaceous solvent such as toluene, at a temperature from −78° C. to 100° C. for a period of 1 to 100 hours; the polymerization is stopped by hydrolysis with ethanol or water, and a diblock copolymer of ethylene and one or more polar comonomers is recovered by filtration and/or extraction by means of a solvent which dissolves the homopolymer of the corresponding polar comonomer. Acetone may be cited as an example.

The present invention equally relates to various applications of the dialkylmagnesiums of the invention or prepared by the process of the invention.

Dialkylmagnesiums can be used as macroinitiators for the polymerization of polar monomers such as those defined above. Diblock copolymers with a polyethylene block are obtained, which are particularly useful as compatibilizing agents for mixtures of the two corresponding homopolymers.

These dialkylmagnesiums can also serve for the manufacture of primary linear fatty alcohols, which are used in the biodegradable-detergent industry, by oxidation and hydrolysis; for the production of α-olefins by thermal decomposition; for the production of acids by reaction with $CO_2$; and to fix a radical of the type R—($CH_2$—$CH_2$)$_n$— on an organic molecule or an active component in order to increase its liposolubility, which is of interest in the pharmaceutical industry.

The following examples illustrate the invention without in any way limiting its scope.

Compounds (I) are given as P—Mg—P' or even MgP$_2$ for the sake of simplicity. BEM denotes n-butylethylmagnesium.

Synthesized P—Mg—P' dialkylmagnesiums, where at least one of P and P' includes a number of carbon atoms greater than 30, have been characterized by gel-permeation chromatography (GPC) after precipitation in ethyl alcohol for hydrolysis, then recovery by filtration, in accordance with the process described below (analysis A).

A sample of 10 cm$^3$ of the reaction medium is introduced into 200 cm$^3$ of ethyl alcohol. The products generated by hydrolysis in accordance with the reaction diagram:

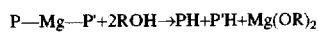

P—Mg—P'+2ROH→PH+P'H+Mg(OR)$_2$ precipitate and are recovered by filtration. washed with 20 cm$^3$ of ethyl alcohol and then dried at 80° C. for 24 hours.

Synthesised P—Mg—P' dialkylmagnesiums, where P and P' each include an average number of carbon atoms between 2 and 30, have been characterized by gas-phase chromatography (GC) after hydrolysis at low temperature under inert atmosphere in accordance with the process described below (analysis B).

A sample of 1 cm$^3$ of the reaction medium is taken and diluted with 10 cm$^3$ of de-oxygenated pentane. The solution obtained is cooled to −20° C., then 5 cm$^3$ of de-oxygenated water is added drop by drop while stirring, and the mixture is left to react for 1 hour. The reaction takes place according to the reaction diagram:

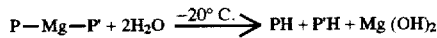

P—Mg—P' + 2H$_2$O $\xrightarrow{-20°\,C.}$ PH + P'H + Mg(OH)$_2$

The organic phase is subsequently recovered by decanting, dried and subjected to gas-phase chromotographic analysis.

Synthesized dialkylmagnesiums have also been identified by reaction with CO$_2$ in accordance with the reaction:

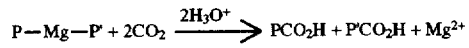

P—Mg—P' + 2CO$_2$ $\xrightarrow{2H_3O^+}$ PCO$_2$H + P'CO$_2$H + Mg$^{2+}$ to form acids which can be characterized by nuclear magnetic-resonance spectroscopy and mass and infra-red spectrometry.

Furthermore alkylation reactions of SnCl$_4$ by dialkylmagnesiums have been carried out in accordance with the following reaction:

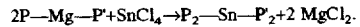

2P—Mg—P'+SnCl$_4$→P$_2$—Sn—P'$_2$+2 MgCl$_2$.

The reaction was carried out at 80° C. for 2 hours in ISOPAR L as the solvent. The resulting product (P$_2$—Sn—P'$_2$) was analyzed by GPC (analysis C).

Dialkylmagnesiums can also be identified by the infra-red spectroscopy of the derivatives obtained by thermolysis. In effect the dialkylmagnesiums, when brought to a high temperature (greater than 125° C.) decompose to α-olefins and magnesium dihydride by a reaction of β hydrogen elimination. Thus the increase in the unsaturation rates during thermolysis can be observed.

These dialkylmagnesiums are in all cases characterized by a number average molecular weight ($\overline{Mn}$), a weight average molecular weight ($\overline{Mw}$) and a polydispersity index ($\overline{Mw}/\overline{Mn}$). The value Mp is also indicated, denoting the molecular mass at the distribution peak. The average number of carbon atoms in each of the two chains bound to the magnesium was calculated on the basis of the $\overline{Mn}$.

Example 1

64.4 mg (0.1 mmole) of Cp*$_2$SmCl$_2$Li(OEt$_2$)$_2$ are placed in solution with 20 cm$^3$ of toluene under inert atmosphere. A quantity of n-butylethylmagnesium is added to this solution to obtain a molar ratio of Mg/Sm=10, and the whole stirred for 2 hours at ambient temperature (20° C.).

A double-walled flask fitted with a stirrer is dried at 120° C. and then purged with argon. 500 cm$^3$ of anhydrous ISOPAR L is placed in it and brought to a temperature of 80° C. The solvent is then saturated with ethylene at a pressure of 1.2 bar. The solution prepared earlier is then injected into the reaction vessel. The ethylene consumption is then registered by flowrators. The reaction is carried out for 5 minutes. The yield of long-chain P—Mg—P' dialkylmagnesium is 4.4 g (i.e. 4.3 g of ethylene has been consumed). The ethylene is then evacuated and replaced by argon. A sample is taken and subjected to analysis A as described above. The molecular masses $\overline{Mn}$, $\overline{Mw}$ and Mp are respectively 1900, 2400 and 2390. The average length of each chain bound to the magnesium is thus 1900/14=136 carbons (cf. Table 1).

Example 2

The operating method of example 1 is reproduced using a quantity of Cp*$_2$SmCl$_2$Li(OEt$_2$)$_2$ of 0.2 mmole and an Mg/Sm ratio of 50, carrying out the polymerization for 54 minutes.

At the end of the 54 minutes the reaction mixture is slightly cooled and the reaction product recovered by filtration on fritted glass. A whitish solid is thus obtained, a sample of which is subjected to analysis A.

The operating method and results of analysis A are also reproduced in Table 1.

Examples 3 to 13

The operating method of example 1 is reproduced, varying the Mg/Sm molar ratio and/or the reaction time as given in Table 1 and using a quantity of Cp*$_2$SmCl$_2$Li(OEt$_2$)$_2$ of 0.05 mmole in the case of Example 11.

The operating method and results of analysis A are also reproduced in Table 1:

TABLE 1

| Examples | Molar ratio Mg/Sm | Reaction time (minutes) | Yield in g of ethylene consumed | $\overline{Mn}$ | $\overline{Mw}$ | Mp | $\overline{Mw}/\overline{Mn}$ | Average number of C atoms in each chain bound to the magnesium |
|---|---|---|---|---|---|---|---|---|
| 1 | 10 | 5 | 4.3 | 1900 | 2400 | 2390 | 1.3 | 136 |
| 2 | 50 | 54 | 30 | 1290 | 1620 | 1370 | 1.3 | 92 |
| 3 | 10 | 5 | 4.7 | 1870 | 2190 | 2190 | 1.2 | 134 |
| 4 | 20 | 5 | 3.3 | 690 | 900 | 800 | 1.3 | 49 |
| 5 | 50 | 5 | 2.9 | 400 | 530 | 490 | 1.3 | 29 |
| 6 | 1000 | 1480 | 93 | 460 | 500 | 560 | 1.1 | 33 |
| 7 | 10 | 1 | 0.8 | 540 | 690 | 560 | 1.3 | 39 |
| 8 | 10 | 2.5 | 2.3 | 970 | 1300 | 1240 | 1.3 | 69 |
| 9 | 10 | 7 | 5.8 | 1640 | 2320 | 2420 | 1.4 | 117 |
| 10 | 10 | 2.5 | 2.23 | 1070 | 1400 | 1400 | 1.3 | 76 |
| 11 | 20 | 5.5 | 2.25 | 980 | 1280 | 1170 | 1.3 | 70 |
| 12 | 100 | 75.3 | 38 | 1050 | 1590 | 1050 | 1.5 | 75 |
| 13 | 10 | 10 | 10.1 | 2120 | 3370 | 3070 | 1.6 | 151 |

A comparison of the respective results from examples 1 and 3 and examples 8 and 10 permits verification that the process in accordance with the invention can be properly reproduced.

A comparison of the results from examples 3, 7, 8 and 9 shows that the molecular weights at the peak (Mp) increase regularly as a function of time while retaining a narrow polydispersity. One might hypothesize that all the chains grow in a similar fashion with time.

A comparison of the results from examples 10 and 11, expressing experiments conducted to isoconversion, shows that the molecular weights of the products manufactured depend directly on the quantity of n-butylethylmagnesium introduced at the outset, not on the quantity of samarium.

We may note (Example 13) that at increased polydispersity values ($\overline{Mw}/\overline{Mn}$) the yield increases (in comparison with Example 1), which indicates the appearance of a second product determined as being polyethylene. These increased polydispersity values correspond to the transition to the second stage as defined above.

Example 14

In this example a detailed study was made of the purity of the products as a function of the reaction stage.

Example 1 is reproduced except that an Mg/Sm molar ratio of 50 is used. The reaction is allowed to reach termination point, samples of 20 cm³ being taken throughout the reaction period. The products obtained from these samples were subjected to analysis A. The results are given in Table 2.

The samples enable the two reaction stages to be distinguished. The first stage consists of samples A to E (P—Mg—P' synthesis proper), while the second includes samples F to J.

It is confirmed that in the course of the same reaction, the number and weight average molecular weights, as well as the peak molecular mass, increase regularly, and that polydispersity remains narrow during the first stage. Starting with sample F, precipitation takes place and polydispersity increases significantly. The shape of the GPC curves shows that distribution becomes bimodal. Once the dialkylmagnesium has precipitated, the reaction continues, producing polyethylene of higher molecular weight. A study of the changing characteristics of the dialkylmagnesiums as a function of time shows that their purity is indeed a function of the point at which the reaction is stopped. The maximum value for molecular weight at the peak of the principal distribution corresponding to polyethylene-free P—Mg—P' dialkylmagnesiums reaches 1240 g/mole. It is therefore possible to synthesize P and P' alkyl chains bound to the magnesium, each containing an average of 81 carbon atoms.

Example 15: Synthesis of MgP$_2$ with the System Cp*$_2$NdCl$_2$Li(OEt$_2$)$_2$+BEM at 80° C.

The operating method of example 14 is reproduced, replacing samarium with neodymium.

The operating conditions and results are given in Table 3.

TABLE 2

| Sample | Time (minutes) | Ethylene flow rate (l/h) | $\overline{Mn}$ | $\overline{Mw}$ | Mp | $\overline{Mw}/\overline{Mn}$ | Average number of C atoms in each chain bound to the magnesium | Yield in g of ethylene compound |
|---|---|---|---|---|---|---|---|---|
| A | 1.6 | 42 | 485 | 590 | 450 | 1.2 | 35 | 1.10 |
| B | 8.3 | 27 | 580 | 700 | 600 | 1.2 | 41 | 5.50 |
| C | 18.3 | 22 | 900 | 1110 | 1070 | 1.2 | 64 | 10.15 |
| D | 20.3 | 41 | 950 | 1200 | 1120 | 1.3 | 68 | 11.05 |
| E | 22.1 | 91 | 1130 | 1710 | 1240 | 1.5 | 81 | 13.50 |
| F | 27.9 | 79 | 1420 | 2620 | 1350 | 1.8 | Precipitation | 23.40 |
| G | 30 | 52 | 1550 | 3030 | 1410 | 2.0 | Precipitation | 26.35 |
| H | 35 | 15 | 1720 | 6470 | 1470 | 3.8 | Precipitation | 29 |
| I | 41 | 6 | 1530 | 6080 | 1410 | 4.0 | Precipitation | 30.10 |
| J | 55 | 0 | 1860 | 10960 | 1480 | 5.9 | Precipitation | 30.70 |

TABLE 3

| Sample | Time (minutes) | Ethylene flow rate (l/h) | $\overline{Mn}$ | $\overline{Mw}$ | Mp | $\overline{Mw}/\overline{Mn}$ | Average number of C atoms in each chain bound to the magnesium | Yield in g of ethylene compound |
|---|---|---|---|---|---|---|---|---|
| A | 5 | 31 | 700 | 880 | 670 | 1.2 | 50 | 2.80 |
| B | 16.6 | 15 | 870 | 1090 | 970 | 1.2 | 62 | 7.70 |
| C | 33.9 | 13 | 1200 | 1500 | 1410 | 1.3 | 86 | 12.45 |
| D | 43.1 | 14 | 1390 | 1750 | 1700 | 1.3 | 99 | 14.70 |
| E | 45.4 | 69 | 1560 | 2080 | 1860 | 1.3 | 111 | 15.85 |
| F | 46.3 | 90 | 1745 | 2675 | 1840 | 1.5 | 125 | 17.40 |
| G | 48.6 | 61 | 2070 | 3600 | 2000 | 1.7 | Precipitation | 20.40 |
| H | 52.1 | 55 | 2540 | 4580 | 2360 | 1.8 | Precipitation | 24.40 |
| I | 96 | 4 | 4400 | 10680 | 7630 | 2.4 | Precipitation | 44.10 |

Example 16: Synthesis of MgP$_2$ with the System Cp*$_2$YCl$_2$Li(OEt$_2$)$_2$+BEM The operating method of example 14 is reproduced, replacing samarium with yttrium with Mg/Y=50.

A single sample was taken after 23 minutes. The quantity of ethylene consumed is 13.5 g. The sample was then subjected to analysis A with the following results:

$\overline{Mn}$=1080

$\overline{Mw}$=1650

Mp=1360

$\overline{Mw}/\overline{Mn}$=1.5

Average number of carbon atoms in each chain bound to Mg=97.

Example 17: Synthesis of MgP$_2$ with the System Cp*$_2$SmCl$_2$Li(OEt$_2$)$_2$+BEM at 40° C.

The operating method of example 14 is reproduced, except that the temperature is 40° C.

The results of analysis A carried out on the sample taken after 8 minutes polymerization are as follows:

$\overline{Mn}$=740

$\overline{Mw}$=890

Mp=700

$\overline{Mw}/\overline{Mn}$=1.2

Average number of carbon atoms in each chain bound to Mg=53

Example 18: Synthesis of MgP$_2$ with the System Cp*$_2$SmCl$_2$Li(OEt$_2$)$_2$+BEM at 60° C.

The operating method of example 14 is reproduced, except that the temperature is 60° C.

The operating conditions and results are given in Table 4.

Example 19: Synthesis of MgP$_2$ Beginning with the System Cp*$_2$SmCl$_2$Li(OEt$_2$)$_2$+BEM at 80° C.

The operating method of example 14 is reproduced, except that xylene is used as the solvent.

The results of analysis A carried out on the sample taken after 1 hour 48 minutes polymerization are as follow:

$\overline{Mn}$=3070

$\overline{Mw}$=4530

Mp=4900

$\overline{Mw}/\overline{Mn}$=1.5

Average number of carbon atoms in each chain bound to Mg=219

Example 20: Synthesis of a Light MgP$_2$ Beginning with the System Cp*$_2$SmcI$_2$Li(OEt$_2$)$_2$+BEM Example 1 is reproduced, except that an Mg/Sm molar ratio of 100 is used and toluene is replaced by heptane. The duration of polymerization is 5 minutes.

The reaction product was isolated by evaporating the heptane to dryness and subjected to analysis B after hydrolysis had been carried out in the conditions indicated. The results are shown in Table 5 (below).

Example 21: Synthesis of a Light MgP$_2$ Beginning with the System Cp*$_2$SmcI$_2$Li(OEt$_2$)$_2$+di-n-hexylmagnesium Example 20 is reproduced, except that an Mg/Sm molar ratio of 134 is used and n-butylethylmagnesium is replaced by di-n-hexylmagnesium. The duration of polymerization is 64.3 minutes.

The reaction product was isolated by evaporating the heptane to dryness and subjected to analysis B after hydrolysis had been carried out in the conditions indicated.

TABLE 4

| Sample | Time (minutes) | Ethylene flow rate (l/h) | $\overline{Mn}$ | $\overline{Mw}$ | Mp | $\overline{Mw}/\overline{Mn}$ | Average number of C atoms in each chain bound to the magnesium | Yield in g of ethylene compound |
|---|---|---|---|---|---|---|---|---|
| A | 5 | 20 | 760 | 900 | 720 | 1.2 | 54 | 1.90 |
| B | 16.6 | 12 | 910 | 1160 | 910 | 1.3 | 65 | 6.10 |
| C | 21.3 | 9 | 990 | 1280 | 1025 | 1.3 | 71 | 7.35 |
| D | 28.7 | 7.5 | 980 | 1270 | 1110 | 1.3 | 70 | 8.70 |
| E | 31.5 | 21 | 1050 | 1440 | 1120 | 1.4 | 75 | 9.40 |
| F | 34.4 | 17 | 1200 | 4630 | 1200 | 3.8 | Precipitation | 10.75 |
| G | 41.7 | 9 | 1400 | 11280 | 1200 | 8.1 | Precipitation | 12.70 |

The results are also shown in Table 5:

TABLE 5

| Linear alkanes produced by hydrolysis of P—Mg—P' number of carbon atoms | Example 20 molar % | Example 21 molar % |
|---|---|---|
| 6 | 24.7 | 3.5 |
| 8 | 26.8 | 7.7 |
| 10 | 22.5 | 14.8 |
| 12 | 12.1 | 23.0 |
| 14 | 6.5 | 14.6 |
| 16 | 4.1 | 11.2 |
| 18 | 1.8 | 8.0 |
| 20 | 0.8 | 5.6 |
| 22 | 0.4 | 4.0 |
| 24 | 0.1 | 2.8 |
| 26 | 0.1 | 2.0 |
| 28 | 0 | 1.5 |
| 30 | 0 | 1.2 |
| 32 | 0 | 0.9 |
| 34 | 0 | 0.7 |

The distribution of molar fractions of the alkanes follows a Poisson law, which is a statistical distribution described by:

$$Xp = \frac{e^{-\lambda} \cdot \lambda^x}{X!}$$

where Xp is the molar fraction with x ethylene insertions and λ is the Poisson distribution coefficient equal to the average number of ethylenes added by Mg—C bonding. The value of λ is 2.35 and 3.54 for the dialkylmagnesiums obtained in Examples 20 and 21 respectively. Poisson's law is known to be characteristic of a very narrow distribution, which confirms the results obtained by the present inventors.

One might also conclude that in the case of Example 21 the results conform very closely to the Poisson distribution, since the initial organomagnesian is symmetrical.

Example 22

Example 1 is reproduced except that the Mg/Sm ratio is 50, the solvent is heptane and the reaction is carried out for 30 minutes. The solvent is then evaporated to dryness and 8.6 g of the product isolated.

Sample No. 1 is subjected to analysis A following hydrolysis by ethyl alcohol.

Sample No. 2 is subjected to thermolysis at 200° C. for 3 hours, then to analysis A following hydrolysis by ethyl alcohol.

Samples 1 and 2 are then analyzed by infra-red spectroscopy to analyze the double bonds of the vinyl, vinylidene and transvinylene types.

The results of analysis A and of infra-red analysis of the unsaturated components are shown in Table 6:

TABLE 6

| Sample | $\overline{Mn}$ | $\overline{Mw}$ | $\overline{Mw}/\overline{Mn}$ | Vinyl | Vinylidene | Trans-vinylene | Total |
|---|---|---|---|---|---|---|---|
| 1 | 696 | 798 | 1.1 | 0.325 | 0.577 | <0.005 | 0.902 |
| 2 | 761 | 921 | 1.2 | 2.518 | 0.479 | 4.445 | 7.442 |

(Double bond for 100° C.)

Example 23

Example 1 is reproduced except that an Mg/Sm molar ratio of 50 is used and the reaction time is 25 minutes.

The results of analysis A and C as defined above are shown in Table 7.

TABLE 7

| Analysis | $\overline{Mn}$ | $\overline{Mw}$ | Mp | $\overline{Mw}/\overline{Mn}$ |
|---|---|---|---|---|
| A | 1025 | 1240 | 1220 | 1.2 |
| C | 2360 | 3580 | 4100 | 1.5 |

Analysis C reveals a bimodal distribution, which is here explained by the fact that the reaction between $MgP_2$ and $SnCl_4$ was incomplete. However, one may remark that the peak molecular mass (Mp) is increased by a factor of 3.5. These results prove that the chains produced by multiple insertion of ethylene are effectively bound to the magnesium.

Example 24: Preparation of an Ethylene/Methyl Methacrylate Copolymer

The conditions of Example 1 are reproduced except that an Mg/Sm ratio of 50 is used.

After 5 minutes polymerization, 20 cm³ of the reaction medium are taken and subjected to analysis A, with the following results:

$\overline{Mn}$=400

$\overline{Mw}$=525

Mp=485

$\overline{Mw}/\overline{Mn}$=1.3

Average number of carbon atoms in each chain bound to Mg=29 and then injected with 50 mmoles of methyl methacrylate.

After 5 minutes the intermediate organometallic product is hydrolyzed in ethanol at the same temperature (80° C.), which stops the reaction. The copolymer is then precipitated by dilution in heptane. 3.2 g of the expected copolymer is recovered by filtration.

Analysis A of this copolymer yielded the following results:

$\overline{Mn}$=720

$\overline{Mw}$=990

Mp=920

$\overline{Mw}/\overline{Mn}$=1.4

Example 25: Preparation of an Ethylene/Methyl Methacrylate Copolymer

The conditions of Example 1 are reproduced except that an Mg/Sm ratio of 50 is used.

After 30 minutes polymerization, 20 cm³ of the reaction medium are taken and subjected to analysis A, with the following results:

$\overline{Mn}$=640

$\overline{Mw}$=880

Mp=710

$\overline{Mw}/\overline{Mn}$=1.4

Average number of carbon atoms in each chain bound to Mg=45

Quantity of ethylene consumed=12.4 g

The reaction medium is then cooled from 80° C. to −78° C. and injected with 150 mmoles of methyl methacrylate. After 2 hours the intermediate organometallic product is hydrolyzed in ethanol at the same temperature (−78° C.), which stops the reaction. The copolymer is then precipitated by dilution in heptane at ambient temperature. 16.7 g of the expected copolymer is recovered by filtration.

A sample of the raw product thus obtained (15.5 g) is extracted at 56° C. for 4 days in a 500 cm$^3$ Kumagawa extraction device with acetone as the solvent. 8.2 g of product are recovered and subjected to analysis A with the following results:

$\overline{Mn}$=890
$\overline{Mw}$=1000
Mp=920
$\overline{Mw}/\overline{Mn}$=1.1

Example 26: Preparation of an Ethylene/Methyl Methacrylate Copolymer

The long-chain dialkylmagnesium prepared in Example 2 is used. The results of subjecting it to analysis A are shown in Table 1.

2 mmoles of this P—Mg—P' are dissolved in 100 cm$^3$ of anhydrous de-oxygenated toluene. The solution is then cooled to −30° C. 100 mmoles of methyl methacrylate are then injected. The reaction is carried out for 48 hours. The polymer is precipitated in pentane and then filtered. A sample of the raw product thus obtained (7.7 g) is extracted at 56° C. for 4 days in a 500 cm$^3$ Kumagawa extraction device with acetone as the solvent. 7.2 g of product are recovered and subjected to analysis A with the following results:

$\overline{Mn}$=1480
$\overline{Mw}$=1940
Mp=1580
$\overline{Mw}/\overline{Mn}$=1.3

Example 27: Preparation of an Ethylene/ε-Caprolactone Copolymer

The conditions of Example 1 are reproduced except that an Mg/Sm ratio of 50 is used.

After 22 minutes polymerization 20 cm$^3$ of the reaction medium are taken and subjected to analysis A, with the following results:

$\overline{Mn}$=1100
$\overline{Mw}$=1325
Mp=1250
$\overline{Mw}/\overline{Mn}$=1.2

Average number of carbon atoms in each chain bound to Mg=79 and at 24 minutes injected with 50 mmoles of ε-caprolactone.

After one hour, the intermediate organometallic product is hydrolyzed in ethanol at the same temperature (80° C.), which stops the reaction.

A sample of the raw product thus obtained (8.6 g) is extracted at 56° C. for 10 days in a 500 cm$^3$ Kumagawa extraction device with acetone as the solvent. 1 g of product is recovered in the cartridge and subjected to analysis A with the following results:

$\overline{Mn}$=1760
$\overline{Mw}$=2230
Mp=2230
$\overline{Mw}/\overline{Mn}$=1.26

The dissolved fraction exhibits a bimodal distribution with a peak corresponding to the ethylene/ε-caprolactone copolymer and a second peak corresponding to the ε-caprolactone homopolymer.

Example 28: Application to the Synthesis of Saturated Carboxylic Acids

The conditions of Example 1 are reproduced except that an Mg/Sm ratio of 50 is used and ISOPAR L is replaced by toluene. Polymerization is carried out for 5 minutes.

Once the polymerization has terminated, the ethylene is eliminated by de-gassing and the solution cooled to 15° C. under argon. $CO_2$ is then bubbled directly into the solution for 20 minutes. Three extractions are then carried out in an aqueous acidic medium ($H_2O$/HCl 5%). The organic phase is recovered and dried on $Na_2SO_4$ for 48 hours with stirring.

After the solution has been concentrated, the raw product is analyzed by mass spectrometry (FAB$^+$). It has been possible to identify molecular ions of m/e from 101 to 297, corresponding to the acids $CH_3$—$(CH_2)_3$—$CO_2H$ to $CH_3$—$(CH_2)_{17}$—$CO_2H$, each separated by a —$CH_2$—$CH_2$— unit (with a mass of 28 g).

Example 29

Example 1 is reproduced except that 0.74 g of diethylene ether (corresponding to $Et_2O$/Mg=2) are added to 0.55 g of n-butylethylmagnesium in solution in 20 cm$^3$ of toluene. After one hour the resulting solution is added to 64.4 mg (0.1 mole) of $Cp^*{}_2SmCl_2Li(OEt_2)_2$ (Mg/Sm=50).

The polymerization is carried out for 1015 seconds at a constant ethylene flow rate equal to 40 l/hr. 13.65 g of long-chain dialkylmagnesium are obtained.

We claim:

1. A long-chain dialkylmagnesium composition represented by formula (I):

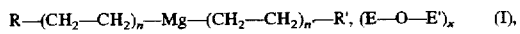

R—(CH$_2$—CH$_2$)$_n$—Mg—(CH$_2$—CH$_2$)$_{n'}$—R', (E—O—E')$_x$    (I), wherein:
 R and R' each independently represent a $C_1$-$C_{20}$ hydrocarbon residue, branched or unbranched, substituted or unsubstituted, of the alkyl, cycloalkyl, or aralkyl type;
 n and n', identical or substantially identical, each represent an average number of —CH$_2$—CH$_2$— linkages such that an average number of carbon atoms in each of the two chains borne by Mg is greater than 20;
 E and E', identical or different, each represent an alkyl radical, linear or cyclical, branched or unbranched; and
 0≦x≦2, wherein x represents an average value of the number of moles of E—O—E' ether complexed to the dialkylmagnesium.

2. A dialkylmagnesium composition in accordance with claim 1, wherein the average number of carbon atoms in each of the two chains borne by Mg is greater than 40.

3. A dialkylmagnesium composition in accordance with one of claim 1 and 2, wherein the dialkylmagnesium composition has a polydispersity index between 1.1 and 2.

4. A process for preparing a dialkylmagnesium represented by formula (I):

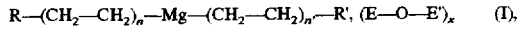

R—(CH$_2$—CH$_2$)$_n$—Mg—(CH$_2$—CH$_2$)$_{n'}$—R', (E—O—E')$_x$    (I), wherein:
 R and R' each independently represent a $C_1$-$C_{20}$ hydrocarbon residue, branched or unbranched, substituted or unsubstituted, of the alkyl, cycloalkyl, or aralkyl type;
 n and n', identical or substantially identical, each represent an average number of —CH$_2$—CH$_2$— linkages such that an average number of carbon atoms in each of the two chains borne by Mg is greater than 2;
 E and E', identical or different, each represent an alkyl radical, linear or cyclical, branched or unbranched; and
 0≦x≦2, wherein x represents an average value of the number of moles of E—O—E' ether complexed to the dialkylmagnesium.

the process comprising:

polymerizing ethylene in an anhydrous de-oxygenated hydrocarbonaceous solvent in the presence of a catalyst represented by formula (II):

$$Cp*_2MCl_2Li(OEt_2)_2 \quad (II),$$

in which:

Cp* represents a pentamethylcyclopentadienyl ligand;

M is scandium, yttrium, or a metal of the lanthanide series; and

Et represents ethyl, and in the presence of a dialkylmagnesium, soluble in the solvent, represented by formula (III):

$$R\text{—}Mg\text{—}R', (E\text{—}O\text{—}E')_x \quad (III),$$

in which R, R', E, E', and x are as defined above, as a chain-transfer agent, wherein the polymerization is carried out at a pressure between 1 to 10 bar and at a temperature between 20° and 120° C.; and stopping the polymerization before polydispersity of a polymer product obtained exceeds 2.

5. A process in accordance with claim 4, wherein an n-butylethylmagnesium or a di-n-hexylmagnesium or a dialkylmagnesium of formula (I) as defined in claim 1 and prepared by the process as defined in claim 4 is used as the dialkylmagnesium of formula (III).

6. A process in accordance with claim 4, wherein M in formula (II) represents samarium, neodymium, or yttrium.

7. A process in accordance with claim 4, wherein M in formula (II) represents samarium, and the Mg/Sm molar ratio is between 5 and 10,000.

8. A process in accordance with claim 4, wherein the solvent is an aliphatic hydrocarbon, linear or cyclical, saturated or unsaturated; or a mixture of heavy alkanes; or an aromatic hydrocarbon, substituted or unsubstituted.

9. A process in accordance with claim 4, wherein the pressure is between 1 and 2 bar.

10. A process in accordance with claim 4, wherein the temperature is between 40° and 80° C.

11. A process in accordance with claim 4, wherein the polymerization is carried out for a period between 2 minutes and 100 hours.

12. A process in accordance with claim 4, wherein the stopping is carried out prior to or at a time when a precipitate corresponding to an increase in ethylene consumption appears.

13. A dialkylmagnesium composition in accordance with one of claim 1 and 2, wherein the dialkylmagnesium composition has a polydispersity index between 1.1 and 1.5.

14. A process in accordance with claim 4, wherein stopping of the polymerization takes place before the polydispersity of the polymer product exceeds 1.5.

15. A process in accordance with claim 7, wherein the Mg/Sm molar ratio is between 30 and 1000.

16. A process in accordance with claim 8, wherein the solvent is an aliphatic hydrocarbon selected from the group consisting of heptane, cyclohexane, decaline, and isodecane.

17. A process in accordance with claim 8, wherein the solvent is a mixture of $C_9$ to $C_{12}$ alkanes.

18. A process in accordance with claim 8, wherein the solvent is an aromatic hydrocarbon selected from the group consisting of toluene, xylene, or mesitylene.

19. A process in accordance with claim 4, wherein the polymerization is carried out for a period between 1 and 3 hours.

* * * * *